(12) United States Patent
Garrigue et al.

(10) Patent No.: US 12,397,148 B2
(45) Date of Patent: Aug. 26, 2025

(54) DEVICE FOR FIXING AND POSITIONING A CARDIAC PUMP

(71) Applicant: FINEHEART, Pessac (FR)

(72) Inventors: Stéphane Garrigue, Begles (FR);
Jean-Baptiste Rousseau, Pessac (FR);
Emmanuel Bougere, Pessac (FR);
Jérémy Collas, Bordeaux (FR)

(73) Assignee: FINEHEART, Pessac (FR)

( * ) Notice: Subject to any disclaimer, the term of this patent is extended or adjusted under 35 U.S.C. 154(b) by 0 days.

(21) Appl. No.: 18/052,381

(22) Filed: Nov. 3, 2022

(65) Prior Publication Data

US 2023/0145482 A1    May 11, 2023

(30) Foreign Application Priority Data

Nov. 10, 2021    (FR) ...................................... 2111957

(51) Int. Cl.
  *A61M 60/861*    (2021.01)
  *A61M 60/17*    (2021.01)
  (Continued)

(52) U.S. Cl.
  CPC .......... *A61M 60/861* (2021.01); *A61M 60/17* (2021.01); *A61M 60/859* (2021.01); *A61M 60/863* (2021.01)

(58) Field of Classification Search
  CPC .. A61M 60/861; A61M 60/17; A61M 60/216; A61M 60/859; A61M 60/863; A61M 60/178
  See application file for complete search history.

(56) References Cited

U.S. PATENT DOCUMENTS

2011/0313237 A1* 12/2011 Miyakoshi .......... A61M 1/3653
  156/173
2013/0261375 A1* 10/2013 Callaway ............ A61M 60/827
  600/16

(Continued)

FOREIGN PATENT DOCUMENTS

DE    102018200974 A1 *  7/2019 .......... A61F 2/2481
FR       3103101         5/2021
(Continued)

OTHER PUBLICATIONS

Vrana, Nihal Engin et al. "Titanium microbead-based porous implants: bead size controls cell response and host integration." Advanced healthcare materials vol. 3,1 (2014): 79-87. doi: 10.1002/adhm. 201200369 (Year: 2014).*

(Continued)

*Primary Examiner* — Jennifer Pitrak McDonald
*Assistant Examiner* — Christine Sison
(74) *Attorney, Agent, or Firm* — Perman & Green, LLP

(57) ABSTRACT

The present document relates to a device for fixing a cardiac pump in an opening of a ventricular wall of a beating heart. The device includes: a hollow main body of overall cylindrical shape having an outer surface, this hollow main body includes a proximal end and a distal end between which said the outer surface extends, at least one portion of the outer surface of the main body intended to be placed inside ventricular cavity, except for its distal end, has a surface relief provided with protuberances and hollows, the distal end of the hollow main body forms a smooth crown having an arithmetic average roughness of less than or equal to 1 μm in order to stop the colonization of the fixing device by endothelial cells.

13 Claims, 5 Drawing Sheets

(51) Int. Cl.
　　　*A61M 60/859*　　　(2021.01)
　　　*A61M 60/863*　　　(2021.01)

(56) References Cited

U.S. PATENT DOCUMENTS

| | | | | |
|---|---|---|---|---|
| 2015/0273124 A1* | 10/2015 | Callaway | ............ | A61M 60/857 |
| | | | | 623/3.26 |
| 2016/0067395 A1* | 3/2016 | Jimenez | .............. | A61M 60/178 |
| | | | | 606/151 |
| 2016/0175501 A1* | 6/2016 | Schuermann | ......... | A61M 60/17 |
| | | | | 600/16 |
| 2018/0256799 A1* | 9/2018 | Matthes | .............. | A61M 60/861 |
| 2021/0170164 A1* | 6/2021 | Wisniewski | ........ | A61M 60/861 |
| 2022/0395680 A1* | 12/2022 | Collas | ................ | A61M 60/865 |

FOREIGN PATENT DOCUMENTS

| | | | | |
|---|---|---|---|---|
| WO | 2010050114 | 5/2010 | | |
| WO | WO-2012019126 A1 * | 2/2012 | .............. | A61M 1/12 |

OTHER PUBLICATIONS

Han, Cheol-Min et al. "The electron beam deposition of titanium on polyetheretherketone (PEEK) and the resulting enhanced biological properties." Biomaterials vol. 31,13 (2010): 3465-70. doi:10.1016/j.biomaterials.2009.12.030 (Year: 2010).*

Mehdizadeh Omrani, Maryam et al. "Polyether ether ketone surface modification with plasma and gelatin for enhancing cell attachment." Journal of biomedical materials research. Part B, Applied biomaterials vol. 109,5 (2021): 622-629. doi:10.1002/jbm.b.34726 (Year: 2020).*

\* cited by examiner

[Fig. 1]
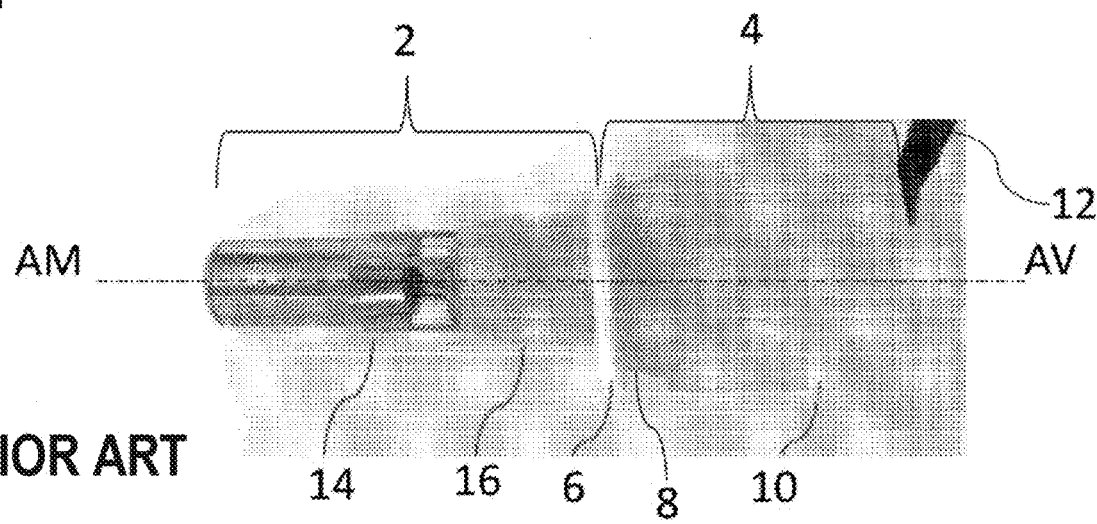
PRIOR ART
[Fig. 2]
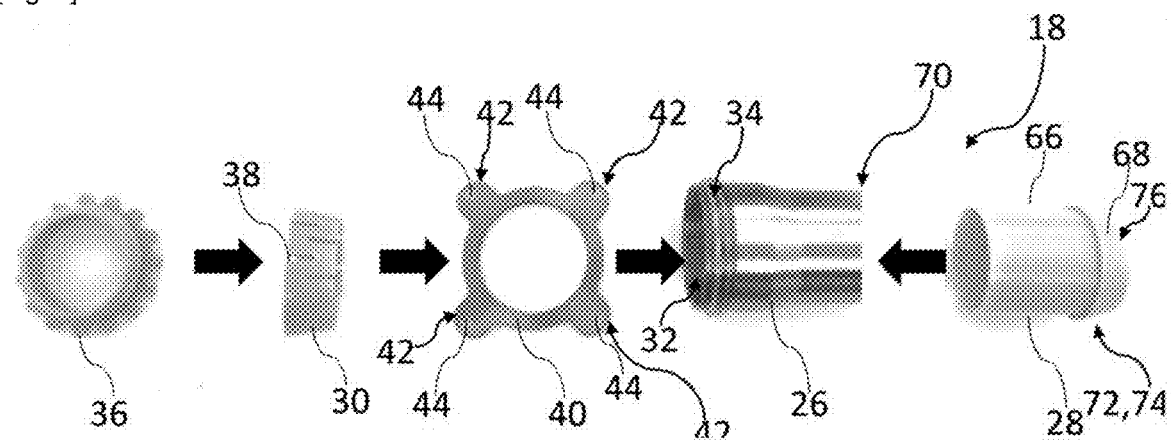
[Fig. 3]
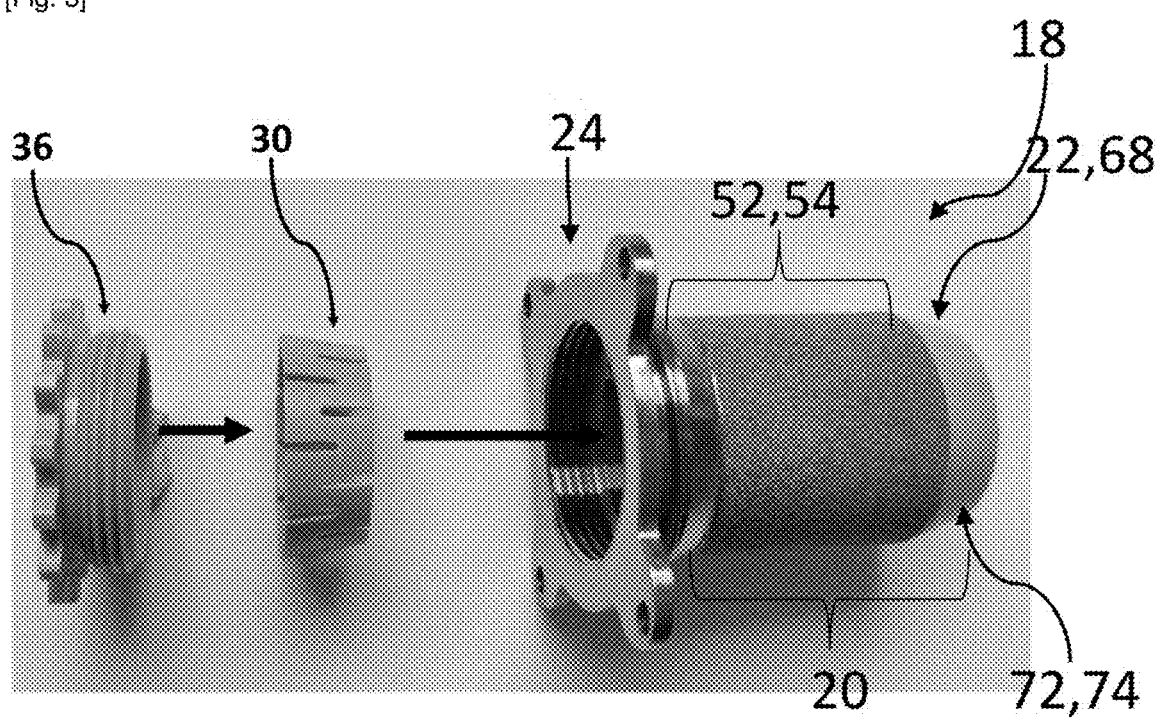

[Fig. 4]
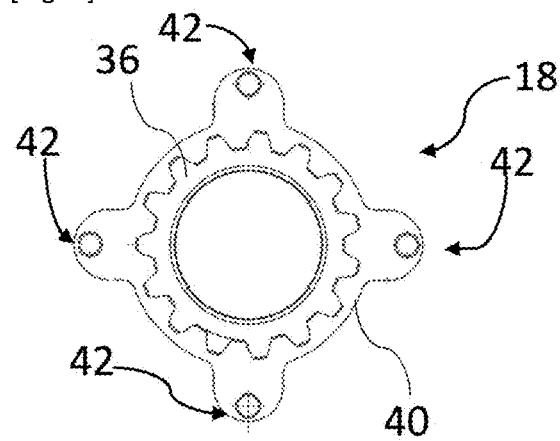
[Fig. 5]
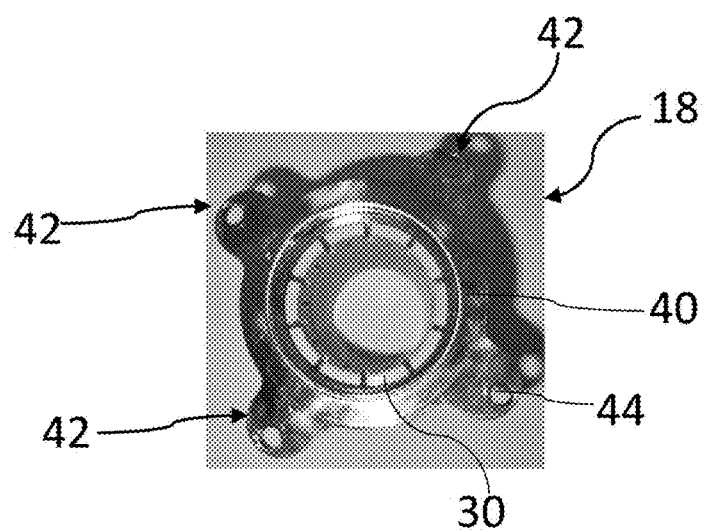
[Fig. 6]
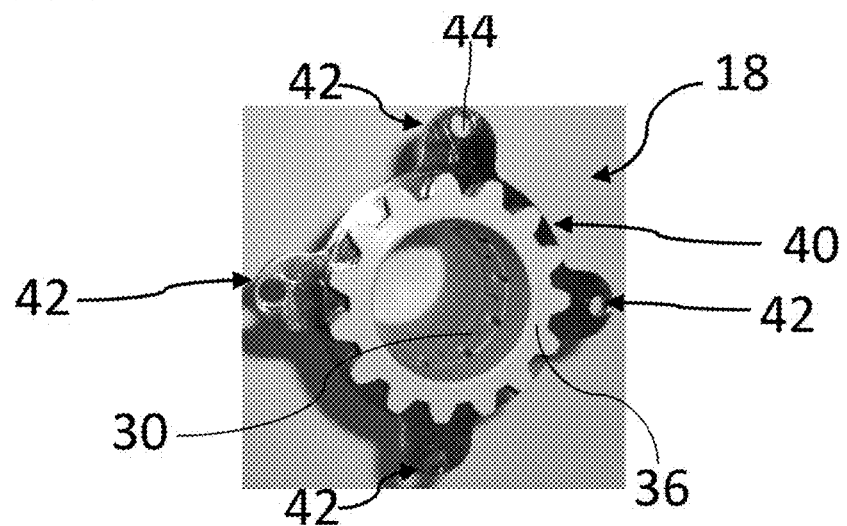

[Fig. 7]
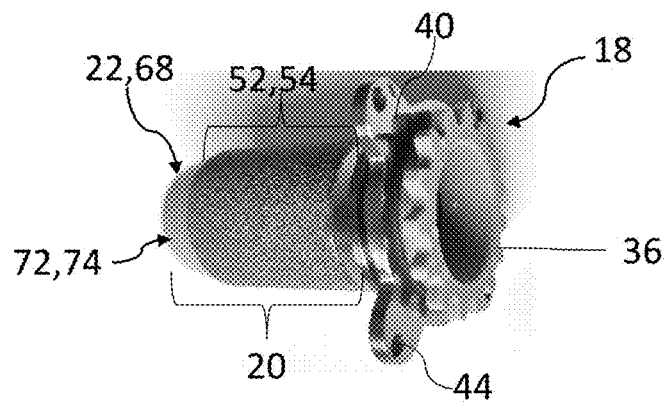
[Fig. 8]
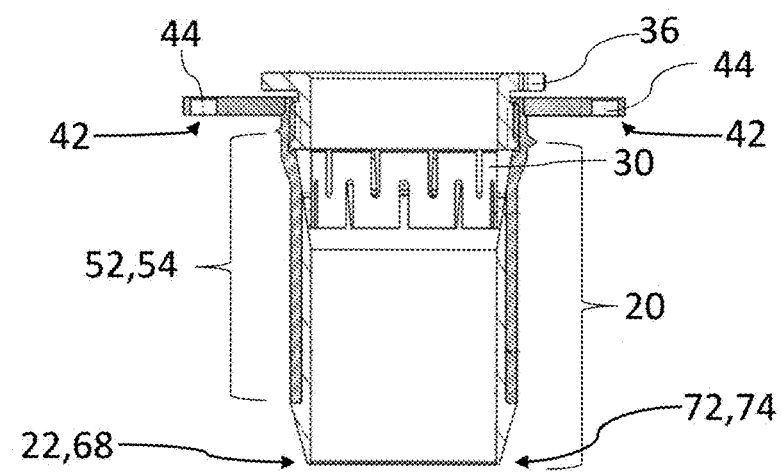
[Fig. 9]
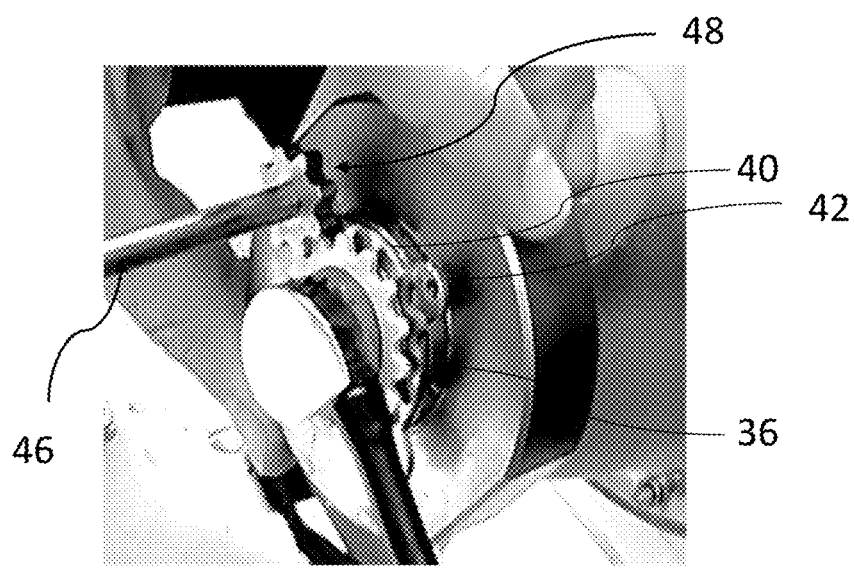

[Fig. 10]
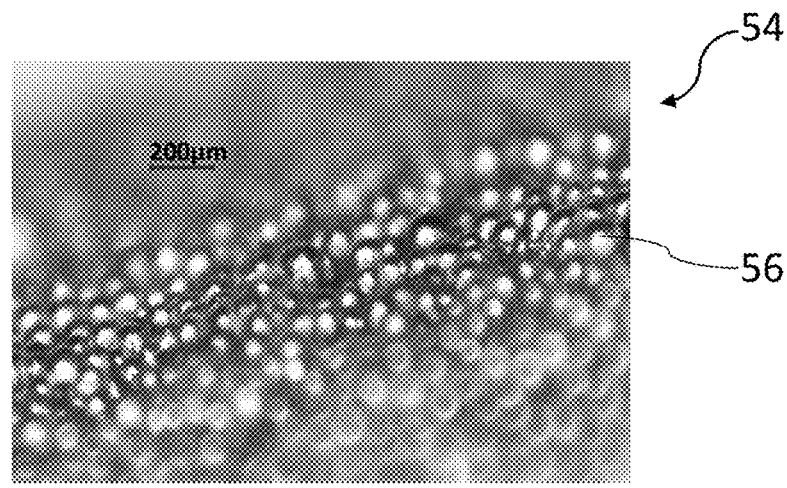
[Fig. 11]
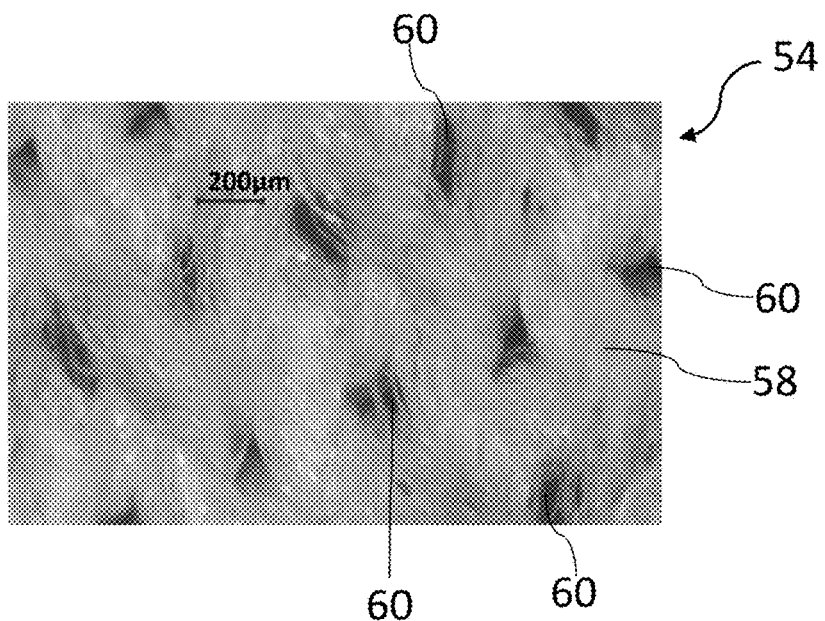
[Fig. 12]
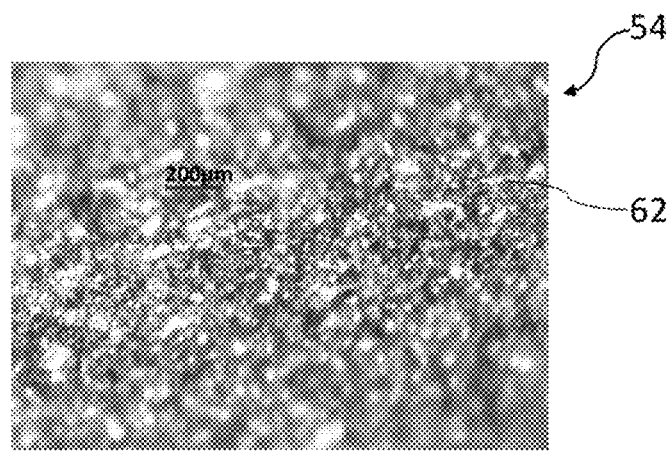

[Fig. 13]
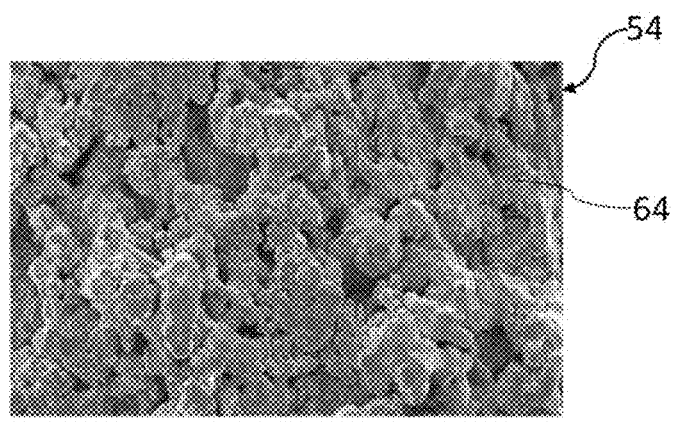
[Fig. 14]
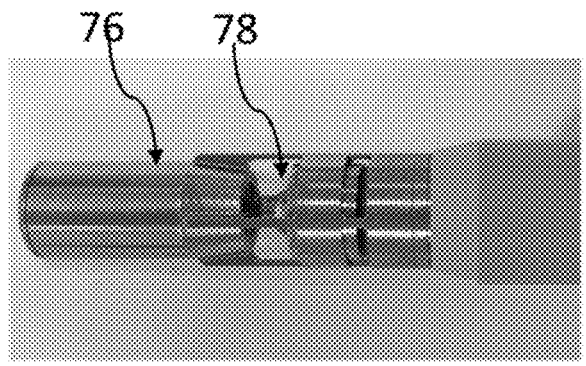

DEVICE FOR FIXING AND POSITIONING A CARDIAC PUMP

CROSS-REFERENCE TO RELATED APPLICATIONS

This application is based on and claims priority under 35 U.S.C. § 119 to French Patent Application No. 2111957, filed on Nov. 10, 2021, in the French Intellectual Property Office, the disclosure of which is incorporated by reference herein in its entirety.

BACKGROUND

Field

The present document relates to the field of cardiac assist pumps.

It relates more particularly to a medical device for fixing a cardiac pump in an opening of a ventricular wall of a beating heart.

Brief Description of Related Developments

Cardiac insufficiency is a pathology in which a patient's heart is unable to deliver a sufficient flow of blood to meet the metabolic requirements of the organism.

Cardiac assist pumps are conventionally used to assist a left ventricle of a heart. It is then referred to as an artificial heart pump. This artificial and mechanical pump does not replace the heart, which continues to function, but provides help to the weakened ventricle in order to increase the blood flow in a manner appropriate to the needs of the individual.

In the case where a transplant is not possible, this cardiac pump is implanted on a long-term basis.

As is illustrated in FIG. 1, the implantable cardiac pumps of the prior art typically comprise an intraventricular part 2 and an extraventricular part 4. In the extraventricular part 4, a medical device with a cardiac pump of the prior art comprises from upstream (AM) to downstream (AV): an attachment flange 6, a connector 8, a removable sheath with non-return valve 10, and a power cable 12. In the intraventricular part 2, this medical device has a cardiac pump 14 and an insert 16 made of polyether ether ketone (PEEK), said insert making it possible to receive, support and orient said cardiac pump 14 with respect to the aortic valve. The upstream and downstream parts are here located with respect to the ventricular wall of the beating heart.

However, with a medical device of this kind, one observes a cellular colonization of the insert 16, which extends to the part protruding from the body of the cardiac pump 14. An obstruction of the blood aspiration orifices of the cardiac pump 14 thus appears over time, leading to poorer performance of the cardiac pump, which can have serious consequences as regards the health of the patient.

There is therefore a pressing need for an insert with which it is possible to overcome the disadvantages of the prior art.

SUMMARY

The present disclosure aims to overcome the disadvantages of the prior art by making available a device for fixing a cardiac pump in an opening of a ventricular wall of a beating heart, which device is simple in design and makes it possible to avoid obstruction of the blood aspiration orifices of the cardiac pump, to maintain the latter in a desired orientation in the ventricular cavity, and to allow the ejection orifice of the cardiac pump to be positioned at a controlled distance from the aortic valve.

The present disclosure also relates to a coating whose properties make it possible to facilitate a covering of tissue and to strengthen the anchoring of the main body of said fixing device.

The present disclosure further relates to the use of a smooth crown which prevents any aggregation of proteins, cells or molecules, and which prevents colonization of the body of the pump by cell tissue within the ventricle.

The present document relates to a device for fixing a cardiac pump in an opening of a ventricular wall of a beating heart, comprising
  a hollow main body of overall cylindrical shape having an outer surface,
  this hollow main body comprising a proximal end and a distal end between which said outer surface extends, said distal end being intended to protrude from said ventricular wall inside the corresponding ventricular cavity of the beating heart,
  at least one portion of the outer surface of said main body intended to be placed inside said ventricular cavity when the proximal end of this fixing device is fixed to said ventricular wall has, except for its distal end, a surface relief provided with protuberances and hollows and made of a material permitting the adherence and growth of endothelial cells, at least said portion of the outer surface comprising a coating covering a surface of titanium or of titanium alloy,
  the distal end of said hollow main body forms a smooth crown having an arithmetic average roughness $R_{max}$ of less than or equal to 1 μm in order to stop the colonization of said fixing device by endothelial cells.

The smooth crown thus makes it possible to create a barrier to the colonization generating a space free of any natural tissue. The result of this is that the openings of the cardiac pump are no longer obstructed, and therefore the cardiac pump is no longer clogged up.

Endothelialization of the coating of the main body is controlled by the surface state of said coating. Endothelialization is understood to mean a colonization by natural cell tissue. The coating of the main body promotes this endothelialization, by virtue of a surface relief provided with protuberances and hollows. This is promoted all the more when the coating is made of titanium or a titanium alloy. In fact, by this technique, the cellular adherence is improved.

An advantage of this endothelialization is to guarantee anchoring and correct orientation of a system composed of main body and cardiac pump. In fact, this endothelialization makes it possible to exert a pressure on the system composed of main body and cardiac pump. This notion of orientation of the body of the cardiac pump is very important since it makes it possible not only to maintain the cardiac pump in place but also to arrange the latter properly and keep it stable with respect to the aortic valve. The pump is thus blocked at the desired depth in the ventricle.

By virtue of this endothelialization, the coating of the main body is additionally preserved from any bacterial attack. The quantity of cell tissue agglomerating on the coating is optimized according to the geometry of the heart, whether this heart has an obtuse or oblique apex.

Said hollow main body can have a first hollow cylindrical body made entirely of titanium or of titanium alloy, said first cylindrical body having, on at least part of its outer surface, said surface covering, a second hollow cylindrical body having an external flange at one end, said second cylindrical body being inserted into said first hollow cylindrical body such that its end is placed in the continuation of said outer surface of the first cylindrical body, forming a surface continuity therewith, said end of the second cylindrical body defining the distal end of said main body.

This arrangement makes it possible not only to maintain the cardiac pump in place but also to arrange the latter properly and keep it stable with respect to the aortic valve.

Said distal end or external flange can have a longitudinal dimension of between 10 mm and 20 mm.

The quantity of cell tissue agglomerating on the coating is optimized according to the geometry of the heart. By virtue of this longitudinal dimension, the case of an obtuse heart is covered.

The distal end or external flange can have a longitudinal dimension of between 2 mm et 10 mm.

The quantity of cell tissue agglomerating on the coating is optimized according to the geometry of the heart. By virtue of this longitudinal dimension, the case of an oblique heart is covered.

Said second cylindrical body can be smooth and made entirely of ceramic or of PEEK (polyether ether ketone).

When the second body is made of PEEK, it is advantageously hydrophobic and inert. This second body is all the more hydrophobic and inert the more its surface is smooth. This second body does not support cell adherence.

An arithmetic average roughness of the coating covering the outer surface made of titanium or of a titanium alloy can be between 100 µm and 300 µm.

The coating of the main body promotes endothelialization, by virtue of the increased surface area of contact or more precisely by virtue of the high arithmetic average roughness.

The proximal end of said main body can have a flared shape delimiting a seat for receiving a clamping ring, the function of which is to clamp annularly around the body of the cardiac pump, the inner wall of said proximal end moreover having a first, inner thread for screwing a toothed nut.

This clamping ring permits leaktightness and holds the toothed nut in place.

An outer wall of the proximal end can have a second, outer thread for receiving a ring comprising at least one lug, preferably four (4), each having an orifice for receiving the end of a clamping tool.

Advantageously, this ring makes it easier for the operator to tighten the toothed nut. As the clamping tool comprises a recess intended to cooperate with the toothed nut, such as teeth complementing the teeth of the toothed nut, the free end of this clamping tool can be inserted into the opening of a lug in such a way that its recess is engaged with the teeth of the toothed nut for the purpose of tightening this nut.

Furthermore, the distal end of said main body can be beveled in order to clamp the body of the cardiac pump inserted in said device, when said at least one part of the outer surface of the main body has been colonized by endothelial cells. The body of the pump is thus held firmly in position.

The geometry of this beveled distal end makes it possible to adapt to the geometry of the beating heart and to permit better orientation of the cardiac pump.

The coating can be formed solely of titanium microspheres.

These titanium microspheres facilitate a tissue covering and solidify or strengthen the anchoring of the main body.

The titanium microspheres can each have a mean diameter of between 100 µm and 300 µm.

This diameter distribution is calculated to increase as far as possible the arithmetic average roughness of the coating.

The coating can alternatively have an openworked woven fabric formed of a plurality of polyester filaments.

The coating can be of the Spondycoat—T317A type.

The outer surface of the coating can also have a scoured surface state. "Scoured surface state" is understood to mean a surface state for which a layer of material of the outer surface is removed, leaving a substrate exposed. For example, the state of this surface could be one that results from sandblasting the outer surface of the coating. During this sandblasting, an abrasive is sprayed at high speed, using compressed air, through a nozzle and onto the outer surface that is to be scoured.

The coating can have protuberances and hollows in a random distribution.

DESCRIPTION OF THE DRAWINGS

Other features, details and advantages will emerge on reading the following detailed description and analyzing the appended drawings, in which:

FIG. 1 shows a cardiac pump according to the prior art.

FIG. 2 shows a first view of an assembly of a fixing device according to the disclosure.

FIG. 3 shows a second view of a partially mounted assembly of the fixing device illustrated in FIG. 2, according to the disclosure.

FIG. 4 shows a view of a ring and a toothed nut of the fixing device, according to the disclosure.

FIG. 5 shows a view, as per FIG. 4, of the fixing device, showing a positioning of a clamping ring, according to the disclosure.

FIG. 6 shows a downstream view of the fixing device with the toothed nut mounted in said fixing device, according to the disclosure.

FIG. 7 shows a side view of the fixing device.

FIG. 8 shows a sectional and schematic view of the fixing device.

FIG. 9 shows the toothed nut fitted against the ring of the fixing device.

FIG. 10 shows a first embodiment of a coating of a fixing tube, according to the disclosure.

FIG. 11 shows a second embodiment of a coating of a fixing tube, according to the disclosure.

FIG. 12 shows a third embodiment of a coating of a fixing tube, according to the disclosure.

FIG. 13 shows a fourth embodiment of a coating of a fixing tube, according to the disclosure.

FIG. 14 shows a cardiac pump according to the disclosure.

DETAILED DESCRIPTION

The drawings and description below essentially contain elements of a certain character. Therefore, they not only may be used to better understand the present disclosure, but also contribute to its definition, where applicable. It will be noted that the figures are not to scale.

The present document relates to a device 18 for fixing a cardiac pump in an opening of a ventricular wall of a beating heart.

As is illustrated in FIGS. 2 to 8, the fixing device 18 has a hollow main body 20 of overall cylindrical shape. This main body 20 comprises a distal end 22 and a proximal end 24. Distal end 22 is understood as the end of the hollow main body 20 farthest away from the ventricular wall of the beating heart. Conversely, proximal end 24 is understood as the end of the hollow main body 20 that is closest to the ventricular wall of the beating heart. The hollow main body 20 comprises a first hollow cylindrical body 26 and a second hollow cylindrical body 28. The first hollow cylindrical body 26 is made of titanium or of a titanium alloy. The second hollow cylindrical body 28 is made entirely of ceramic or of PEEK (polyether ether ketone).

The first cylindrical body 26 of the main body 20 comprises, at the proximal end 24, a flared shape delimiting an inner seat. The flared shape can be conical, for example. The seat delimits a space inside the first cylindrical body 26 of the main body 20 able to receive a clamping ring 30. This clamping ring 30 is able to deform, so as to conform to an inner wall of the first cylindrical body 26 of the main body 20 in proximity to said proximal end 24.

At the proximal end 24, the first cylindrical body 26 has a first, inner thread 32 and a second, outer thread 34. The first, inner thread 32 of the first cylindrical body 26 is configured to receive a toothed nut 36 that can be screwed into said first, inner thread 32 and come into contact with an end 38 of the clamping ring 30. The second, outer thread 34 of the first cylindrical body 26 is configured to receive a ring 40. This ring 40 can be screwed along said second, outer thread 34. The ring 40 has four lugs 42. These lugs 42 each have a receiving orifice 44 for a clamping tool 46. As is illustrated in FIG. 89, the clamping tool 46 has a free end 48 that cooperates with the toothed nut 36.

An outer surface 52 of the first cylindrical body 26, excluding the distal end 22 of this first cylindrical body 26, has a coating 54. This coating 54 has a surface relief provided with a random distribution of protuberances and hollows. This coating, covering the outer surface 52 of the first cylindrical body 26 except for the distal end 22, has a parameter of arithmetic average roughness of between 100 µm and 300 µm.

In a particular embodiment illustrated in FIG. 10, this coating 54 can comprise a plurality of layers of microspheres 56 of titanium. These microspheres 56 of titanium have a mean diameter of between 100 µm and 300 µm. This coating 54 has a surface relief characterized by an arithmetic average roughness of between 100 and 300 µm. These microspheres 56 are sprayed onto the outer surface 52 of the first cylindrical body 26, excluding the distal end. The microspheres 56 are bound to the outer surface 52 by heating to a temperature close to the melting point of titanium. No binder is used to hold the microspheres 56 together.

In a particular embodiment illustrated in FIG. 11, this coating 54 can comprise an openworked woven fabric 58 formed of a plurality of polyester filaments. The filaments have a mean diameter of between 250 µm and 350 µm. This woven fabric has openings 60 with a mean diameter of between 50 µm and 100 µm.

In a particular embodiment illustrated in FIG. 12, the coating 54 can have a scoured surface state 62. The result of this scouring is that a granularity is present at the surface, increasing the surface area of contact between said coating and the blood circulating in the left ventricle of the heart. This granularity can be quantified in terms of arithmetic average roughness. The arithmetic average roughness of said coating is between 100 and 300 µm. This scouring is obtained by sandblasting.

In a particular embodiment illustrated in FIG. 13, the outer surface has received a surface treatment. The coating is composed of PEEK that has received a plasma spray. Traditionally, plasma is a partially ionized gas composed of atoms, molecules, ions and excited free radicals, following stimulation by radio frequencies, microwaves or electron discharge. This plasma spray is configured to influence a hydrophilic/hydrophobic character, a charge and a surface roughness. The coating can be of the Spondycoat 64—T317A type.

The second cylindrical body 28 is able to be inserted inside the first hollow cylindrical body 26 such that a first part 66 is in contact against an inner surface of the second hollow cylindrical body 26 and a second part 68 protrudes from a distal end 70 of the first hollow cylindrical body 26, this distal end 70 of the first cylindrical body 26 being opposite the second, outer thread 34. This second part 68 of the second cylindrical body 28 forms the distal end 22 of the main body 20. This second part 68 has an external flange 72. This external flange 72 comprises a smooth crown 74. This smooth crown 74 has an arithmetic average roughness Rmax of less than or equal to 1 µm in order to stop the colonization of said fixing device 18 by endothelial cells. The distal end 22 of the main body 20, hence the smooth crown 74, is beveled. This beveled smooth crown 74 is configured to clamp the cardiac pump 76. As is illustrated in FIG. 14, the cardiac pump 76 is inserted from the side of the toothed nut 36, passes inside the main body 20 and emerges from the side of the smooth crown 74.

A longitudinal dimension by which the smooth crown 74 extends depends on a span of the heart and on a thickness of a wall of said heart. Longitudinal dimension is understood as a space between the distal end 70 of the first cylindrical body 26 and a distal end 76 of the smooth crown 74. It can also be referred to as a depth of the smooth crown 74.

The depth of the smooth crown is between 2 and 10 mm, if the heart has a very obtuse apex at the end of contraction. In fact, during contraction, there is then very little contact between the smooth crown and the wall of the heart.

By contrast, the depth of the smooth crown 74 is between 10 et and 20 mm if the heart has a very obtuse apex at the end of contraction. In fact, the increase in the depth of the smooth crown 74 is configured to avoid a situation where the walls of the heart are not in contact with this smooth crown 74. There is therefore no deposition of cells on said smooth crown 74.

During operation, the smooth crown 74 makes it possible to create a barrier to the colonization generating a space free of any natural tissue. In fact, the smooth crown 74 made of PEEK is hydrophobic and inert. This smooth crown 74 is all the more hydrophobic and inert the more its surface is polished; the distal end of the smooth crown 74 will not support cellular adherence. The result of this is that openings 78 of the cardiac pump 76 are no longer obstructed, and therefore the cardiac pump 76 is no longer clogged up.

Endothelialization of the coating 54 of the first cylindrical body 26 is controlled by the surface state of said coating 54. Endothelialization is understood to mean a colonization by natural cell tissue. The coating 54 of the first cylindrical body 26 promotes endothelialization by virtue of the increased surface area of contact or more precisely by virtue of the high arithmetic average roughness. In fact, by this technique, the cellular adherence is improved. The advantage of this endothelialization is to reinforce the correct orientation of a system composed of main body 20 and cardiac pump 76. In fact, this endothelialization makes it possible to exert a pressure on the system composed of main body 20 and cardiac pump 76. This notion of orientation of the body of the cardiac pump 76 is very important since it makes it possible not only to maintain the cardiac pump 76 in place but also to arrange the latter properly and keep it stable with respect to an aortic valve. By virtue of this endothelialization, the coating 54 of the first cylindrical body 26 is preserved from any bacterial attack. The quantity of cell tissue agglomerating on the coating 54 is optimized according to the geometry of the heart, whether this heart has an obtuse or oblique apex.

The use of the second cylindrical body 28 makes it possible to avoid scratching the cardiac pump 76 while using a softer material.

What is claimed is:

1. A device, for fixing a cardiac pump in an opening of a ventricular wall of a beating heart, comprising:
    a hollow main body of overall cylindrical shape having an outer surface,
    this hollow main body comprising a proximal end and a distal end between which said outer surface extends, said distal end being intended to protrude from said ventricular wall inside the corresponding ventricular cavity of the beating heart,
    at least one portion of the outer surface of said main body intended to be placed inside said ventricular cavity, except for its distal end, has a surface relief provided with protuberances and hollows and made of a material permitting the adherence and growth of endothelial cells, at least said portion of the outer surface comprising a coating covering a surface of titanium or of titanium alloy, and
    the distal end of said hollow main body forms a smooth crown having an arithmetic average roughness of less than or equal to 1 µm in order to stop the colonization of said fixing device by endothelial cells,
    wherein said hollow main body has:
        a first hollow cylindrical body made entirely of titanium or of titanium alloy, wherein said first cylindrical body has, on at least part of its outer surface, said surface coating,
        a second hollow cylindrical body having an external flange at its end, wherein said second cylindrical body is inserted into said first hollow cylindrical body such that its end is placed in the continuation of said outer surface of the first cylindrical body, forming a surface continuity therewith,
        and wherein:
            the outer surface of the portion of the external flange in contact with the first cylindrical body and the outer surface of the portion of the first cylindrical body in contact with the external flange is flush,
            the rest of the outer surface of said external flange has a diameter equal to and/or less than the diameter of the outer surface of the first cylindrical body,
            said end of the second cylindrical body defines the distal end of said main body,
            an opening defined by the hollow main body being configured to receive a propulsive cardiac pump body,
            said end of the second cylindrical body being configured to maintain in position said propulsive cardiac pump body when inserted; and
        wherein said second cylindrical body is made of PEEK (polyether ether ketone) and has an entirely smooth surface with an arithmetic mean roughness Rmax of less than or equal to 1 µm, so as to prevent said second cylinder body from scratching of the propulsive cardiac pump.

2. The device according to claim 1, in which said distal end or external flange has a longitudinal dimension of between 10 mm and 20 mm.

3. The device according to claim 1, in which the distal end or external flange has a longitudinal dimension of between 2 mm and 10 mm.

4. The device according to claim 1, in which an arithmetic average roughness of the coating covering the outer surface made of titanium or of a titanium alloy is between 100 µm and 300 µm.

5. The device according to claim 1, in which the proximal end of said main body has a flared shape delimiting a seat for receiving a clamping ring to clamp annularly around the body of the cardiac pump, the inner wall of said proximal end having a first, inner thread for screwing a toothed nut.

6. The device according to claim 5, in which an outer wall of the proximal end has a second, outer thread for receiving a ring comprising at least one lug having an orifice for receiving the end of a clamping tool.

7. The device according to claim 1, in which the distal end of said main body is beveled in order to clamp the body of the cardiac pump inserted in said device.

8. The device according to claim 1, in which the coating is formed solely of titanium microspheres.

9. The device according to claim 8, in which the titanium microspheres each have a mean diameter of between 100 µm and 300 µm.

10. The device according to claim 1, in which the coating has an open worked woven fabric formed of a plurality of polyester filaments.

11. The device according to claim 1, in which the coating is a plasma spray.

12. The device according to claim 1, in which the outer surface of the coating has a scoured surface state.

13. The device according to claim 1, in which the coating has protuberances and hollows in a random distribution.

* * * * *